United States Patent
Seow et al.

(10) Patent No.: US 11,045,273 B2
(45) Date of Patent: Jun. 29, 2021

(54) ELASTIC SURGICAL INTERFACE FOR ROBOTIC SURGICAL SYSTEMS

(71) Applicant: Covidien LP, Mansfield, MA (US)

(72) Inventors: Chi Min Seow, New Haven, CT (US); Michael Zemlok, Prospect, CT (US); Robert Allen, Shelton, CT (US)

(73) Assignee: Covidien LP, Mansfield, MA (US)

( * ) Notice: Subject to any disclaimer, the term of this patent is extended or adjusted under 35 U.S.C. 154(b) by 85 days.

(21) Appl. No.: 15/763,138

(22) PCT Filed: Sep. 22, 2016

(86) PCT No.: PCT/US2016/053002
§ 371 (c)(1),
(2) Date: Mar. 26, 2018

(87) PCT Pub. No.: WO2017/053507
PCT Pub. Date: Mar. 30, 2017

(65) Prior Publication Data
US 2019/0053866 A1 Feb. 21, 2019

Related U.S. Application Data

(60) Provisional application No. 62/232,623, filed on Sep. 25, 2015.

(51) Int. Cl.
*A61B 46/10* (2016.01)
*A61B 34/35* (2016.01)
(Continued)

(52) U.S. Cl.
CPC .............. *A61B 46/10* (2016.02); *A61B 34/30* (2016.02); *A61B 34/35* (2016.02); *A61B 34/71* (2016.02);
(Continued)

(58) Field of Classification Search
CPC ... A61B 46/10; A61B 34/35; A61B 17/00234; A61B 2017/00477; A61B 2034/302; A61B 34/30; A61B 34/71
(Continued)

(56) References Cited

U.S. PATENT DOCUMENTS 10,188,385 B2 * 1/2019 Kerr ..................... A61B 17/068
2005/0096661 A1 5/2005 Farrow et al.
(Continued)

FOREIGN PATENT DOCUMENTS

CN 104394793 A 3/2015
CN 104546139 A 4/2015
(Continued)

OTHER PUBLICATIONS

International Search Report and Written Opinion issued in International Application No. PCT/US2016/053002 dated Jan. 4, 2017.
(Continued)

*Primary Examiner* — Kawing Chan
*Assistant Examiner* — Zemenay T Truneh
(74) *Attorney, Agent, or Firm* — Carter DeLuca & Farrell LLP

(57) ABSTRACT

A sterile barrier assembly includes a linear drive section and a rotation drive section. The linear drive section includes a corrugated portion interfacing with an axial output of an instrument driving unit on a non-sterile side and an engaging portion interfacing with a tool assembly of a surgical instrument on a sterile side. The rotational drive section includes a first engaging portion interfacing with a rotational output of the instrument driving unit on the non-sterile side and a second engaging portion interfacing with the tool assembly of the surgical instrument on the sterile side.

21 Claims, 4 Drawing Sheets

(51) Int. Cl.
*A61B 34/30* (2016.01)
*A61B 34/00* (2016.01)
A61B 17/00 (2006.01)

(52) U.S. Cl.
CPC .............. *A61B 17/00234* (2013.01); *A61B 2017/00477* (2013.01); *A61B 2034/302* (2016.02)

(58) Field of Classification Search
USPC ...................................................... 318/568.2
See application file for complete search history.

(56) References Cited

U.S. PATENT DOCUMENTS

| | | | |
|---|---|---|---|
| 2007/0137371 A1 | 6/2007 | Devengenzo et al. | |
| 2008/0167663 A1 | 7/2008 | De Mathelin et al. | |
| 2009/0248039 A1* | 10/2009 | Cooper | A61B 34/30 606/130 |
| 2010/0268249 A1 | 10/2010 | Stuart | |
| 2010/0274087 A1 | 10/2010 | Diolaiti et al. | |
| 2011/0245833 A1 | 10/2011 | Anderson | |
| 2011/0277775 A1 | 11/2011 | Holop et al. | |
| 2012/0116416 A1 | 5/2012 | Neff et al. | |
| 2013/0035537 A1 | 2/2013 | Wallace et al. | |
| 2014/0069437 A1 | 3/2014 | Reis et al. | |
| 2015/0133960 A1 | 5/2015 | Lohmeier et al. | |
| 2015/0142012 A1 | 5/2015 | Lohmeier et al. | |
| 2015/0148817 A1 | 5/2015 | Lohmeier et al. | |
| 2015/0164593 A1 | 6/2015 | Lohmeier et al. | |
| 2015/0173729 A1* | 6/2015 | Lohmeier | A61B 17/00 606/1 |
| 2018/0168760 A1* | 6/2018 | Koch, Jr. | A61B 17/00234 |
| 2019/0298461 A1* | 10/2019 | Holop | G16H 40/63 |

FOREIGN PATENT DOCUMENTS

| | | |
|---|---|---|
| WO | 2011149187 A2 | 12/2011 |
| WO | 2013075204 A1 | 5/2013 |
| WO | 2015052629 A1 | 4/2015 |

OTHER PUBLICATIONS

Extended European Search Report issued in Application No. 16849557.0, dated Jun. 3, 2019.
First Office Action issued in Chinese Patent Application No. 201680054083.X, dated Apr. 27, 2020.
Second Office Action issued in Chinese Patent Application No. 201680054083.X, dated Oct. 16, 2020.

* cited by examiner

ELASTIC SURGICAL INTERFACE FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2016/053002, filed Sep. 22, 2016, which claims the benefit of and priority to U.S. Provisional Patent Application Ser. No. 62/232,623, filed Sep. 25, 2015, the entire disclosure of which is incorporated by reference herein.

BACKGROUND

Robotic surgical systems have been used in minimally invasive medical procedures. Some robotic surgical systems include a console supporting a robot arm and a surgical instrument that is mounted to the robot arm. The robot arm provides mechanical power to the surgical instrument for its operation and movement. Each robot arm may include an instrument drive unit that is operatively connected to the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument.

The utilization is subject to strict sterility requirements between the patient (in the sterile field) and certain components of the robotic surgical system (out of the sterile field). In order to achieve proper sterility nevertheless, sterile plastic or rubber covers, so-called sterile barriers, are generally pulled over the (inherently non-sterile) device, or are used to give the device a sterile covering.

Therefore, there is a need for a sterile barrier assembly that provides for an easier removal and attachment to the robotic surgical system.

SUMMARY

The present disclosure describes robotic devices, systems, and methods that demonstrate a practical approach to meeting the performance requirements and overcoming the usability challenges associated with sterilization of the robotic devices. In general, the present disclosure describes robotic surgical systems that include an instrument drive unit and a surgical instrument coupled to the instrument drive unit. The surgical instrument includes an end effector controllable to perform surgery in response to telemanipulation of actuators in the instrument drive unit. The instrument drive unit includes a sterile barrier assembly. Utilization of elastic material as the primary material in the sterile barrier assembly enables transmission of movement from one or more actuators in one or more directions.

In accordance with an embodiment of the present disclosure, there is provided a sterile barrier assembly including a linear drive section and a rotational drive section. The linear drive section includes a corrugated portion interfacing with an axial output of an instrument driving unit on a non-sterile side and an engaging portion interfacing with a tool assembly of a surgical instrument on a sterile side. The rotational drive section includes a first engaging portion interfacing with a rotational output of the instrument driving unit on the non-sterile side and a second engaging portion interfacing with the tool assembly of the surgical instrument on the sterile side.

In an embodiment, the corrugated portion may be configured to transition between an elongated state and a contracted state, while providing a fluid tight seal between the instrument driving unit on the non-sterile side and the surgical instrument on the sterile side. In particular, the corrugated portion may include a bellows. In addition, the corrugated portion may have a varying thickness. In an embodiment, the corrugated portion may include slack that tautens as the engaging portion of the linear drive section moves in one direction.

In another embodiment, the corrugated portion may define a recess configured to interface with the axial output of the instrument driving unit.

In another embodiment, the engaging portion of the linear drive section may be adjacent the recess of the corrugated portion.

In an embodiment, the linear drive section may be monolithically or integrally formed. In addition, the rotational drive section may also be monolithically or integrally formed. In particular, the sterile barrier assembly may be formed of an elastic material.

In an embodiment, the sterile barrier assembly may further include support walls formed of a relatively rigid material to facilitate linear transition of the corrugated portion between the contracted and elongated states.

In accordance with another embodiment of the present disclosure, there is provided a robotic surgical system. The robotic surgical system includes a sterile instrument, a non-sterile drive unit, and a sterile barrier assembly. The sterile instrument has a surgical tool manipulatable by a plurality of tool drivers in a plurality of directions. The non-sterile drive unit includes a plurality of driven outputs. The sterile barrier assembly is partitioned into a sterile side coupled to the sterile instrument and a non-sterile side coupled to the non-sterile drive unit. The sterile barrier assembly includes a linear drive section and a rotational drive section. The linear drive section includes a corrugated portion interfacing with one of the plurality of driven outputs of the non-sterile drive unit and an engaging portion interfacing with one of the plurality of tool drivers of the sterile instrument. The rotational drive section includes a first engaging portion interfacing with one of the plurality of driven outputs of the non-sterile drive unit and a second engaging portion interfacing with one of the plurality of tool drivers of the sterile instrument.

In an embodiment, the corrugated portion may be configured to transition between an elongated state and a contracted state corresponding to an axial displacement of one of the plurality of driven outputs of the non-sterile drive unit.

In an embodiment, one of the plurality of driven outputs of the non-sterile drive unit may impart translational movement to one of the plurality of tool drivers of the sterile instrument. In addition, one of the plurality of driven outputs of the non-sterile drive unit may impart rotation to one of the plurality of tool drivers of the sterile instrument.

In another embodiment, the sterile barrier assembly may be formed of at least one of silicone, nitrile rubber, neoprene, vinyl, latex, or EPDM.

In another embodiment, the sterile barrier assembly may provide a fluid tight seal between the sterile side and the non-sterile side.

DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
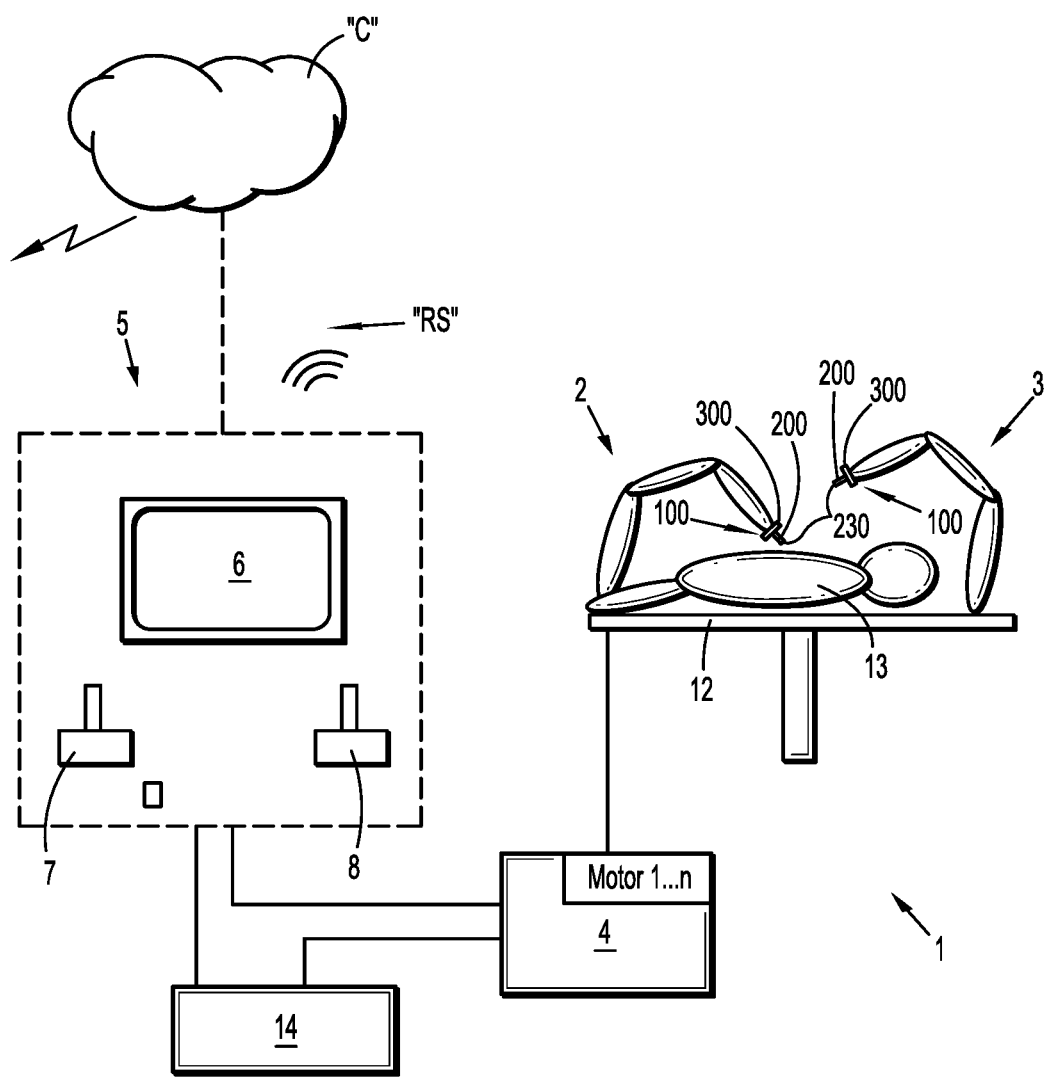
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

With reference to FIG. 1, there is provided a robotic surgical system 1 including a plurality of robotic arms 2, 3; a control device 4; and an operating console 5 coupled with control device 4. Operating console 5 includes a display device 6 and manual input devices 7, 8, by means of which a clinician is able to telemanipulate robotic arms 2, 3.

Each of the plurality of robotic arms 2, 3 includes a plurality of members, which are connected through joints. Robotic surgical system 1 also includes a surgical assembly 100 connected to a distal end of each of robotic arms 2, 3. Surgical assembly 100 includes an instrument drive unit 300 and a surgical instrument 200 detachably coupled to instrument drive unit 300. Surgical instrument 200 includes an end effector 230.

Robotic arms 2, 3 may be driven by electric drives (not shown) that are connected to control device 4. Control device 4 (e.g., a computer) is set up to activate the drives, in particular by means of a computer program, in such a way that surgical assembly 100 of respective robotic arms 2, 3 executes a desired movement according to a movement defined by means of manual input devices 7, 8. Control device 4 may also be set up in such a way that it regulates movement of robotic arms 2, 3 and/or of the drives.

With continued reference to FIG. 1, robotic surgical system 1 is configured for use on a patient 13 lying on a patient table 12 for a minimally invasive procedure by means of end effector 230. Robotic surgical system 1 may include more than two robotic arms 2, 3. The additional robotic arms may also be connected to control device 4 and may be telemanipulatable by means of operating console 5. One or more additional surgical assemblies 100 and/or surgical instruments 200 may also be attached to the additional robotic arm.

Control device 4 may control a plurality of motors (Motor 1 . . . n) with each motor configured to drive a pushing or a pulling of one or more cables coupled to end effector 230 of surgical instrument 200. While cables are shown and described, it is contemplated that cables can be replaced with rods or the like. In use, as these cables are pushed and/or pulled, the cables effect operation and/or movement of end effector 230 of surgical instrument 200. It is contemplated that control device 4 coordinates the activation of the various motors (Motor 1 . . . n) to coordinate a pushing or a pulling motion of one or more cables in order to coordinate an operation and/or movement of one or more end effectors 230. In embodiments, each motor can be configured to actuate a drive rod or a lever arm to effect operation and/or movement of end effectors 230 in addition to, or instead of, one or more cables.

Control device 4 can include any suitable logic control circuit adapted to perform calculations and/or operate according to a set of instructions. Control device 4 can be configured to communicate with a remote system "RS," either via a wireless (e.g., Wi-Fi™, Bluetooth®, LTE™, etc.) and/or wired connection. Remote system "RS" can include data, instructions and/or information related to the various components, algorithms, and/or operations of robotic surgical system 1. Remote system "RS" can include any suitable electronic service, database, platform, cloud "C", or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS." Reference may be made to U.S. Patent Publication No. 2012/0116416, filed on Nov. 3, 2011, entitled "Medical Workstation," the entire content of which is incorporated herein by reference, for a detailed discussion of the construction and operation of robotic surgical system 1.

Figure 2:
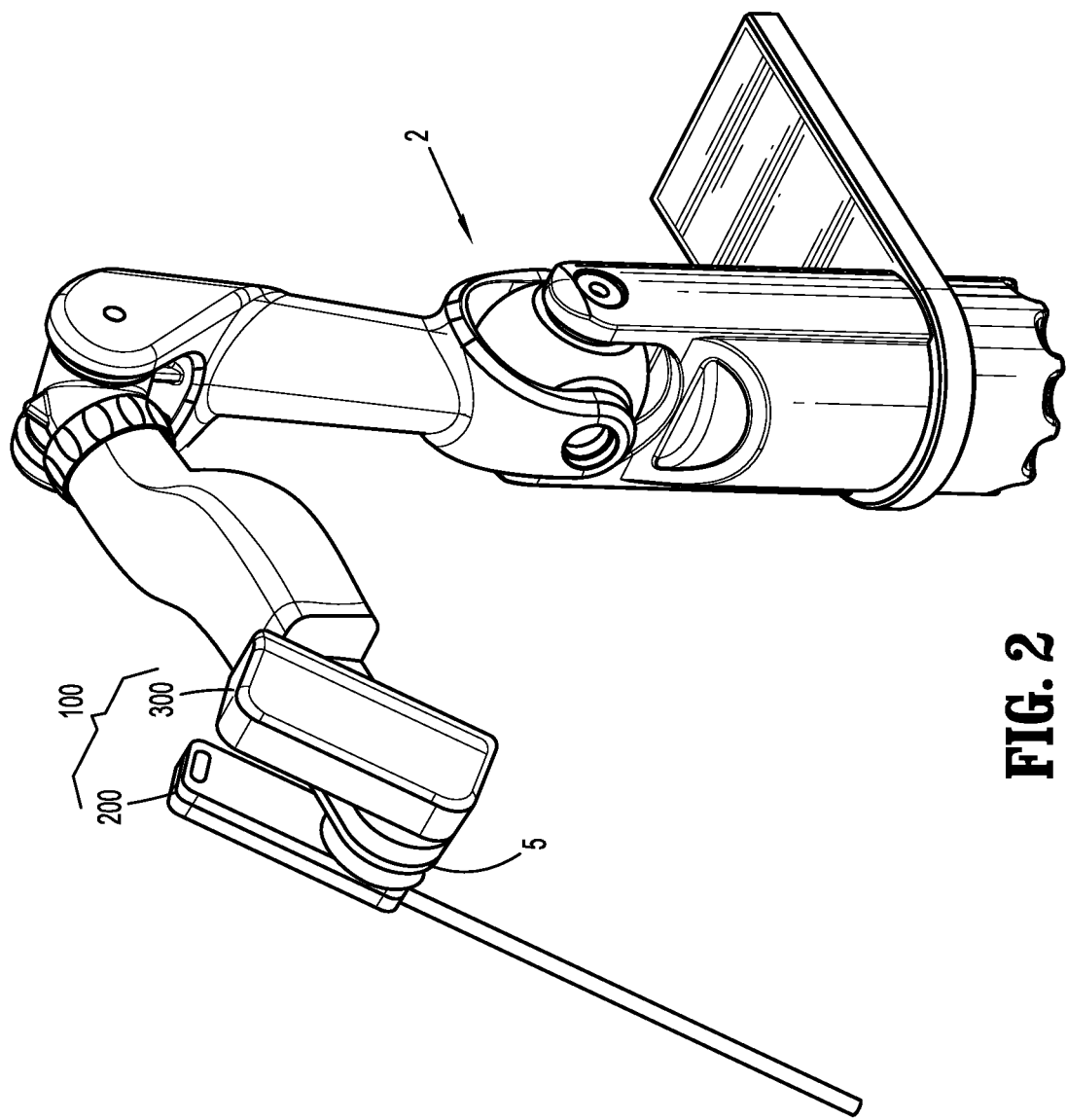
FIG. 2 is a perspective view of a robotic arm having a surgical assembly mounted thereon.
Figure 3:
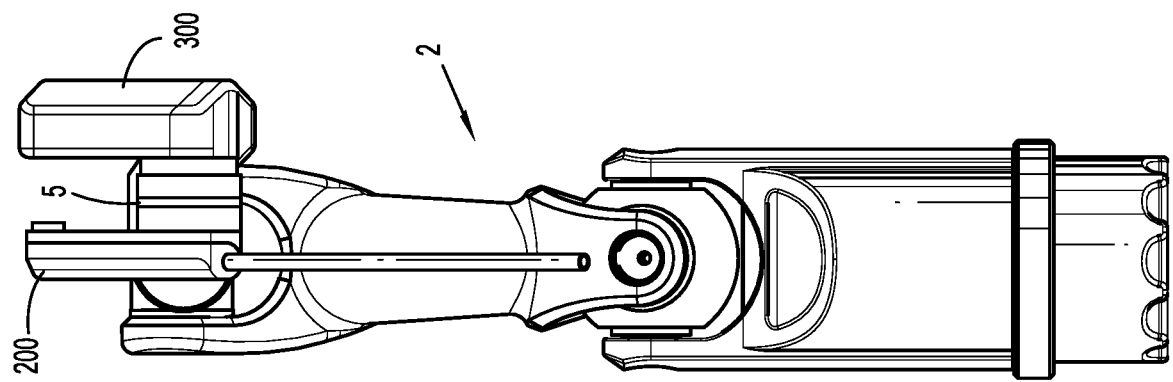
FIG. 3 is a front view of the robotic arm and the surgical assembly of FIG. 2.
Figure 4:
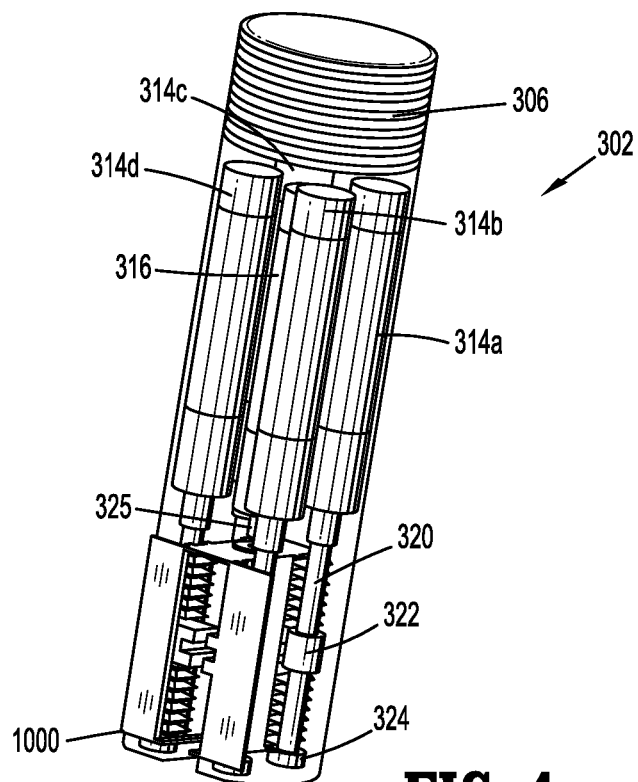
FIG. 4 is a perspective view of an actuator assembly of an instrument drive unit of the robotic surgical system of FIG. 1 with a portion of the actuator assembly removed illustrating a sterile barrier assembly for use in the actuator assembly.

Turning now to FIGS. 2 and 3, instrument drive unit 300 is coupled to a mount 5 (FIG. 3) of robotic arm 2, and surgical instrument 200 is operatively coupled to instrument drive unit 300. With reference now to FIG. 4, instrument drive unit 300 includes an actuation assembly 302 supporting a plurality of actuators or motors 314a, 314b, 314c, 314d, 316 and motor control boards 306 operatively coupled to the plurality of motors 314a, 314b, 314c, 314d, 316. Actuation assembly 302 further includes a sterile barrier assembly 1000 in accordance with an embodiment of the present disclosure. Sterile barrier assembly 1000 establishes a fluid tight seal between a sterile portion of surgical instrument 200 and a non-sterile portion of actuation assembly 302 of instrument drive unit 300.

Each motor 314a, 314b, 314c, 314d is coupled to a respective lead screw 320 rotatably supported on actuation assembly 302 by a bearing 324. Each lead screw 320 includes a linear drive nut 322 threadably mounted thereon. Under such a configuration, rotation of lead screw 320 by respective motor 314a, 314b, 314c, 314d causes axial translation of linear drive nut 322 on lead screw 320, as will be described hereinbelow. Motor 316 is coupled to a lead screw 325. In this manner, rotational output of motors 314a, 314b, 314c, 314d causes axial displacement of linear drive nut 322, and rotational output of motor 316 causes rotation of lead screw 325.

Figure 5:
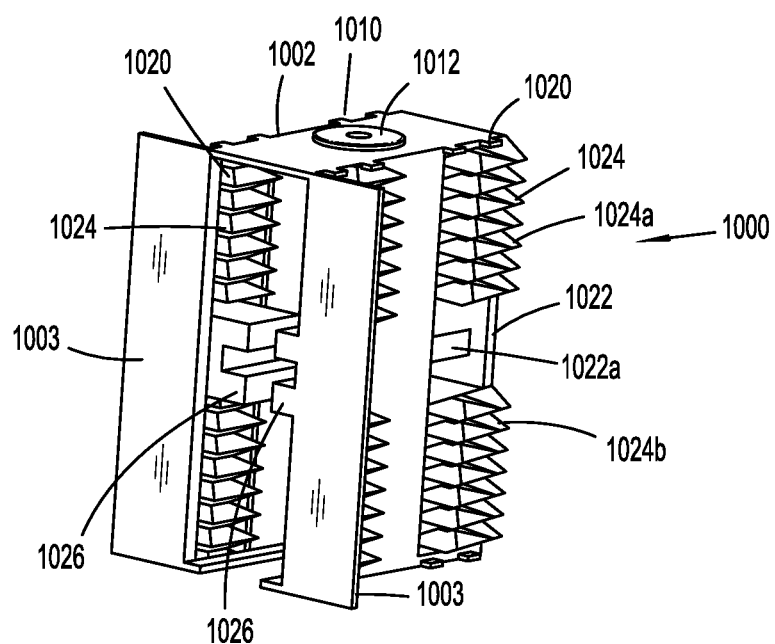
FIG. 5 is a perspective view of the sterile barrier assembly of FIG. 4.

With reference now to FIGS. 4 and 5, sterile barrier assembly 1000 is releasably placed in actuation assembly 302 to separate a sterile portion of surgical instrument 200 with a non-sterile portion of actuation assembly 302, while enabling transmission of linear and/or rotational motion of lead screws 320, 325 in one or more directions. Sterile barrier assembly 1000 includes a base frame 1002 that is formed of an elastic or a pliable material. For example, sterile barrier assembly 1000 may be formed of, e.g., silicone, nitrile rubber, neoprene, vinyl, latex, and EPDM. In particular, sterile barrier assembly 1000 may be formed as a single construct. Alternatively, base frame 1002 may include multiple components that are laminated, overlapped, bonded, glued, interlocked or ultrasonically welded. For example, multi-shot molding techniques may be utilized in instances in which multiple materials are used in combination.

Base frame 1002 includes mounting walls 1003 configured to support base frame 1002 in actuation assembly 302. Mounting walls 1003 may include plastic, metal, ceramic or any other material that provides structural reinforcement or rigidity to isolate respective motions of lead screws 320, 325 and/or to increase or limit movement of linear drive sections 1020. Base frame 1002 further includes a rotational drive section 1010 configured to transmit rotational output of motor 316 to surgical instrument 200 and linear drive sections 1020 configured to transmit respective axial motion of lead screws 320 to surgical instrument 200. Base frame 1002 may be monolithically or integrally formed. Alternatively, linear drive section 1020 or rotational drive section 1010 may be monolithically or integrally formed.

With particular reference to FIG. 5, rotational drive section 1010 includes engaging portions 1012 (only one shown in FIG. 5) configured to operatively engage lead screw 325 coupled to motor 316. Engaging portions 1012 receive lead screw 325 in a sealing relation. Engaging sections 1012 may be monolithically or integrally formed with base frame 1002. For example, at least one of base frame 1002 or engaging portions 1012 may have reduced thickness or stiffness to facilitate rotation of engaging portions 1012 of rotational drive section 1010. Alternatively, engaging portions 1012 may be formed as separate components that rotate within bores (not shown) defined in base frame 1002. In this manner, rotation of lead screw 325 imparts concomitant rotation to the corresponding rotational actuation interface member of surgical instrument 200.

With continued reference to FIG. 5, each of linear drive sections 1020 is configured to operatively engage respective lead screws 320 of motors 314a, 314b, 314c, 314d. Each of linear drive sections 1020 includes a securing portion 1022, a convoluted or corrugated portion 1024, and an engaging portion 1026 disposed adjacent securing portion 1022. Corrugated portion 1024 is transitionable between an elongated state and a contracted state. Corrugated portion 1024 may include, e.g., bellows or spiral configuration. Corrugated portion 1024 includes first and second portions 1024a, 1024b. Securing portion 1022 of linear drive section 1020 is interposed between first and second portions 1024a, 1024b of corrugated portion 124. Securing portion 1022 defines a cavity 1022a configured and dimensioned to securely receive linear drive nut 322 (FIG. 4) therein, such that axial movement of linear drive nut 322 along lead screw 320 transitions corrugated portion 1024 between contracted and elongated states, which, in turn, causes axial movements of engaging portion 1026.

Corrugated portion 10224 includes slack that tautens as engaging portion 1026 of the linear drive section 1020 moves in one direction. Corrugated portion 1024 may provide slack to inhibit an undesirable pulling force being applied to first and second portions 1024a, 1024b of linear drive section 1020. Linear drive nut 322 is threadably mounted on lead screw 320 such that rotation of lead screw 320 causes axial movement of linear drive nut 322 on lead screw 320. Under such a configuration, axial movement of linear drive nut 322 causes contraction or elongation of first and second portions 1024a, 1024b.

Engaging portion 1026 of linear drive section 1020 is disposed adjacent securing portion 1022 to provide concomitant axial movement with linear drive nut 322. Further, engaging portion 1026 of linear drive section 1020 is configured to engage a linear actuation interface member (not shown) of surgical instrument 200 to transmit axial movement to the linear actuation interface member. In this manner, axial movement of linear drive nut 322 imparts concomitant axial movement to engaging portion 1026 of linear drive section 1020, which, in turn, transmits the axial motion to the corresponding linear actuation interface member of surgical instrument 200.

In operation, with reference to FIGS. 3 and 4, instrument drive unit 300 is mounted on mount 5 of robotic arm 2, and surgical instrument 200 is detachably coupled to instrument drive unit 300. Each linear drive nut 322 of actuation assembly 302 securely engages respective securing portion 1022 of respective linear drive section 1020 of sterile barrier assembly 1000. Engaging portion 1026 of each linear drive section 1020 is operatively coupled with the respective linear actuation interface member of surgical instrument 200. Further, lead screw 325 is operatively coupled with a rotational actuation interface member of surgical instrument 200. With surgical instrument 200 operatively coupled to instrument drive unit 300, one or more of the plurality of motors 314a, 314b, 314c, 314d are activated to rotate one or more of lead screws 320, which, in turn, causes translation of one or more engaging portions 1026 of sterile barrier assembly 1000. Actuation of one or more engaging portions 1026 causes translation of corresponding linear actuation interface members of surgical instrument 200. In addition, actuation of motor 316 causes rotation of lead screw 325, which, in turn, imparts rotation to the rotational actuation interface member of surgical instrument 200. Actuation of the rotational or linear actuation interface members of surgical instrument 200 or combinations thereof, imparts movement (e.g., rotation, pivoting, articulation, longitudinal/lateral translation, etc.) to end effector 230 (FIG. 1), or portions thereof.

Although the illustrative embodiments of the present disclosure have been described herein with reference to the accompanying drawings, the above description, disclosure, and figures should not be construed as limiting, but merely as exemplifications of particular embodiments. For example, corrugated portion 1024 of each linear drive section 1020 may have varying thickness. It is to be understood, therefore, that the disclosure is not limited to those precise embodiments, and that various other changes and modifications may be effected therein by one skilled in the art without departing from the scope or spirit of the disclosure.

What is claimed is:

1. A sterile barrier assembly comprising:
   a linear drive section including:
      a corrugated portion interfacing with an axial output of an instrument driving unit on a non-sterile side, the corrugated portion defining a longitudinal axis, the corrugated portion including ridges and grooves arranged along the longitudinal axis of the corrugated portion, the corrugated portion transitionable between an elongated state and a contracted state, with respect to the longitudinal axis of the corrugated portion, the corrugated portion separated into first and second parts along the longitudinal axis of the corrugated portion; and
      an engaging portion disposed along the longitudinal axis and interposed between the first and second parts of the corrugated portion, the engaging portion transmitting axial movement along the longitudinal axis to a tool assembly of a surgical instrument on a sterile side; and
   a rotational drive section including:
      an engaging part interfacing with a rotational output of the instrument driving unit on the non-sterile side, the rotational drive section interfacing with the tool assembly of the surgical instrument on the sterile side.

2. The sterile barrier assembly according to claim 1, wherein the corrugated portion is configured to transition between the elongated state and the contracted state, while providing a fluid tight seal between the instrument driving unit on the non-sterile side and the surgical instrument on the sterile side.

3. The sterile barrier assembly according to claim 2, further comprising support walls formed of a relatively rigid material to facilitate linear transition of the corrugated portion between the contracted and elongated states.

4. The sterile barrier assembly according to claim 1, wherein the corrugated portion includes a bellows.

5. The sterile barrier assembly according to claim 1, wherein the corrugated portion defines a recess configured to interface with the axial output of the instrument driving unit.

6. The sterile barrier assembly according to claim 5, wherein the engaging portion of the linear drive section is adjacent the recess of the corrugated portion.

7. The sterile barrier assembly according to claim 1, wherein the corrugated portion has a varying thickness.

8. The sterile barrier assembly according to claim 1, wherein the linear drive section is monolithically or integrally formed.

9. The sterile barrier assembly according to claim 1, wherein the rotational drive section is monolithically or integrally formed.

10. The sterile barrier assembly according to claim 1, wherein the sterile barrier assembly is formed of an elastic material.

11. The sterile barrier assembly according to claim 10, wherein the corrugated portion includes slack that tautens as the engaging portion of the linear drive section moves in one direction.

12. The sterile barrier assembly according to claim 1, wherein the corrugated portion includes the ridges and grooves in both the elongated and contracted states.

13. A robotic surgical system comprising:
   a sterile instrument having a surgical tool manipulatable by a plurality of tool drivers in a plurality of directions;
   a non-sterile drive unit including a plurality of driven outputs; and
   a sterile barrier assembly partitioned into a sterile side coupled to the sterile instrument and a non-sterile side coupled to the non-sterile drive unit, the sterile barrier assembly including:
      a linear drive section including:
         a corrugated portion interfacing with one of the plurality of driven outputs of the non-sterile drive unit, the corrugated portion including ridges and grooves arranged along a longitudinal axis of the corrugated portion, the corrugated portion transitionable between an elongated state and a contracted state, with respect to the longitudinal axis of the corrugated portion, the corrugated portion separated into first and second parts along the longitudinal axis of the corrugated portion; and
         an engaging portion interposed between the first and second parts of the corrugated portion and axially movable along the longitudinal axis of the corrugated portion, the engaging portion interfacing with one of the plurality of tool drivers of the sterile instrument; and
      a rotational drive section including:
         an engaging part interfacing with one of the plurality of driven outputs of the non-sterile drive unit, the rotational drive section interfacing with one of the plurality of tool drivers of the sterile instrument.

14. The surgical system according to claim 13, wherein the corrugated portion has varying thickness.

15. The surgical system according to claim 13, wherein the elongated state and the contracted state of the corrugated portion correspond to an axial displacement of one of the plurality of driven outputs of the non-sterile drive unit.

16. The surgical system according to claim 15, wherein one of the plurality of driven outputs of the non-sterile drive unit imparts rotation to one of the plurality of tool drivers of the sterile instrument.

17. The surgical system according to claim 13, wherein one of the plurality of driven outputs of the non-sterile drive unit imparts translational movement to one of the plurality of tool drivers of the sterile instrument.

18. The surgical system according to claim 13, wherein the sterile barrier assembly is formed of at least one of silicone, nitrile rubber, neoprene, vinyl, latex, or EPDM.

19. The surgical system according to claim 13, wherein the sterile barrier assembly is integrally formed.

20. The surgical system according to claim 13, wherein the sterile barrier assembly provides a fluid tight seal between the sterile side and the non-sterile side.

21. The surgical system according to claim 13, wherein the corrugated portion is a bellows.

* * * * *